United States Patent
Osawa

(10) Patent No.: US 9,320,497 B2
(45) Date of Patent: Apr. 26, 2016

(54) ULTRASOUND DIAGNOSTIC APPARATUS AND METHOD OF PRODUCING ULTRASOUND IMAGE

(75) Inventor: Atsushi Osawa, Ashigara-kami-gun (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 13/601,391

(22) Filed: Aug. 31, 2012

(65) Prior Publication Data

US 2013/0079640 A1 Mar. 28, 2013

(30) Foreign Application Priority Data

Sep. 27, 2011 (JP) ................................. 2011-210434

(51) Int. Cl.
*A61B 8/00* (2006.01)
*A61B 8/08* (2006.01)

(52) U.S. Cl.
CPC ............. *A61B 8/5207* (2013.01); *A61B 8/4477* (2013.01)

(58) Field of Classification Search
CPC .......... A61B 8/00; A61B 8/44; A61B 8/4483; A61B 8/4488; A61B 8/4494
See application file for complete search history.

(56) References Cited

U.S. PATENT DOCUMENTS

| | | |
|---|---|---|
| 5,172,343 A | 12/1992 | O'Donnell |
| 5,549,111 A | 8/1996 | Wright et al. |
| 7,372,775 B2 * | 5/2008 | Hayashi .......................... 367/138 |
| 2004/0138565 A1 * | 7/2004 | Trucco ............................. 600/447 |
| 2010/0312106 A9 * | 12/2010 | Blalock et al. ................. 600/437 |
| 2011/0077520 A1 * | 3/2011 | Osawa ............................ 600/443 |

FOREIGN PATENT DOCUMENTS

| | | |
|---|---|---|
| JP | 05237117 A | 9/1993 |
| JP | 10506800 A | 7/1998 |
| JP | 2005-058321 A | 3/2005 |

OTHER PUBLICATIONS

Notification of Reasons for Refusal, dispatched Sep. 17, 2013, issued in corresponding JP Application No. 2011-210434, 5 pages in English and Japanese.
Chinese Office Action corresponding to Chinese Patent Application No. 201210320131.9, issued Dec. 31, 2014, 14 pages in Chinese and Englsih.

* cited by examiner

Primary Examiner — Mark Remaly
(74) Attorney, Agent, or Firm — Sughrue Mion, PLLC

(57) ABSTRACT

An ultrasound diagnostic apparatus includes a transducer array having a plurality of transducers arranged in an array, a transmission circuit which supplies an actuation signal to each transducer of the transducer array to transmit an ultrasonic wave toward a subject, a reception circuit which corrects a reception signal output from each transducer having received an ultrasonic echo from the subject in accordance with an angle between a reflection point in the subject and an acoustic radiation surface in each transducer to produce sample data, and an image producer which produces an ultrasound image on the basis of a sound ray signal obtained through phasing addition of sample data produced by the reception circuit.

7 Claims, 5 Drawing Sheets

ULTRASOUND DIAGNOSTIC APPARATUS AND METHOD OF PRODUCING ULTRASOUND IMAGE

BACKGROUND OF THE INVENTION

The present invention relates to an ultrasound diagnostic apparatus and a method of producing an ultrasound image, and in particular, to an ultrasound diagnostic apparatus which performs transmission and reception of ultrasonic waves using a plurality of transducers arranged in an array.

An ultrasound diagnostic apparatus using an ultrasound image has hitherto been put into practical use in the field of medicine. In general, in this type of ultrasound diagnostic apparatus, an ultrasonic beam from a transducer array of an ultrasound probe is transmitted toward a subject, an ultrasonic echo from the subject is received by the transducer array of the ultrasound probe, and the reception signals are electrically processed to produce an ultrasound image.

Normally, after the reception signals obtained by the transducer array of the ultrasound probe are detected, phase matching is performed to produce sample data. An image signal for displaying an ultrasound image is created on the basis of the sample data.

At this time, reception signal detection and phase matching have been performed on the basis of the frequency characteristics of the ultrasound probe in a main lobe maximum sound pressure direction.

On the other hand, since the transducer array of the ultrasound probe has a plurality of transducers arranged in a one-dimensional or two-dimensional array, the angle between one reflection point in the subject and an acoustic radiation surface in each transducer differs between the transducers, and an ultrasonic echo from the reflection point enters a plurality of transducers at different angles. For this reason, the reception signals obtained by the plurality of transducers are different in center frequency, bandwidth, sensitivity, or the like depending on the incidence angle of the ultrasonic echo. Accordingly, phase matching of such reception signals results in degradation in image quality of an ultrasound image.

For example, JP 2005-58321 A discloses an ultrasound diagnostic apparatus in which, when compound scanning is performed to synthesize reception data obtained through transmission/reception of an ultrasonic beam at different transmission/reception angles to obtain an ultrasound image, a center frequency is adjusted in accordance with the transmission/reception angle of an ultrasonic wave, thereby achieving improvement in image quality of the ultrasound image.

However, in the apparatus disclosed in JP 2005-58321 A, the center frequency is changed uniformly in accordance with the angle of the ultrasonic beam in transmission/reception with respect to a plurality of transducers. This is effective for compound scanning in which an ultrasonic beam is transmitted and received at different transmission/reception angles. Meanwhile, there is no effect when an ultrasonic echo from the same reflection point enters the individual transducers at different angles.

SUMMARY OF THE INVENTION

The invention has been accomplished in order to solve the drawbacks in the prior art, and an object of the invention is to provide an ultrasound diagnostic apparatus and a method of producing an ultrasound image capable of suppressing degradation in image quality of an ultrasound image due to the fact that the angle between the reflection point in the subject and the acoustic radiation surface in each transducer of the transducer array differs between the transducers.

An ultrasound diagnostic apparatus according to the present invention comprises:
a transducer array having a plurality of transducers arranged in an array;
a transmission circuit which supplies an actuation signal to each transducer of the transducer array to transmit an ultrasonic wave toward a subject;
a reception circuit which corrects a reception signal output from each transducer having received an ultrasonic echo from the subject in accordance with an angle between a reflection point in the subject and an acoustic radiation surface in each transducer to produce sample data; and
an image producer which produces an ultrasound image on the basis of a sound ray signal obtained through phasing addition of sample data produced by the reception circuit.

A method of producing an ultrasound image according to the present invention comprises the steps of:
supplying an actuation signal to each transducer of a transducer array to transmit an ultrasonic wave toward a subject;
correcting a reception signal output from each transducer having received an ultrasonic echo from the subject in accordance with an angle between a reflection point in the subject and an acoustic radiation surface in each transducer to produce sample data; and
producing an ultrasound image on the basis of a sound ray signal obtained through phasing addition of the produced sample data.

DETAILED DESCRIPTION OF THE INVENTION

Hereinafter, embodiments of the invention will be described with reference to the accompanying drawings.

Embodiment 1

Figure 1:
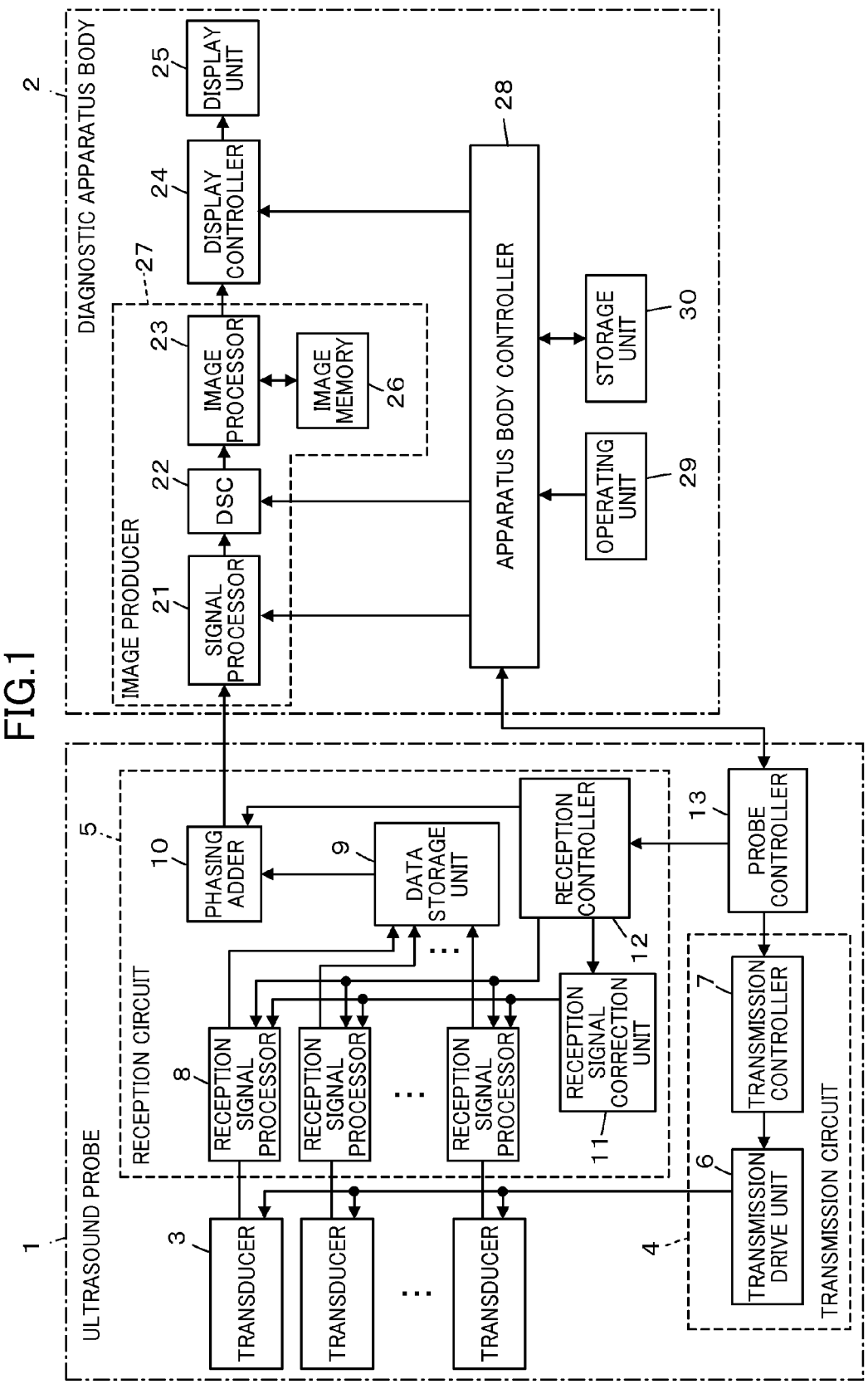
FIG. 1 is a block diagram illustrating a configuration of an ultrasound diagnostic apparatus according to Embodiment 1 of the invention.

FIG. 1 illustrates a configuration of an ultrasound diagnostic apparatus according to Embodiment 1. The ultrasound diagnostic apparatus includes an ultrasound probe 1, and a diagnostic apparatus body 2 connected to the ultrasound probe 1.

The ultrasound probe 1 has a plurality of transducers 3 arranged in a one-dimensional or two-dimensional array. A transmission circuit 4 and a reception circuit 5 are connected to the transducers 3.

The transmission circuit 4 has a transmission drive unit 6 connected to the transducers 3, and a transmission controller 7 connected to the transmission drive unit 6.

The reception circuit 5 has reception signal processors 8 correspondingly connected to the transducers 3, and a phasing adder 10 is connected to the reception signal processors 8 through a data storage unit 9. A reception signal correction unit 11 is connected to each of the reception signal processors 8, and a reception controller 12 is connected to the reception signal processors 8, the phasing adder 10, and the reception signal correction unit 11.

A probe controller 13 is connected to the transmission controller 7 of the transmission circuit 4 and the reception controller 12 of the reception circuit 5.

The diagnostic apparatus body 2 has a signal processor 21 connected to the phasing adder 10 of the ultrasound probe 1, and a DSC (Digital Scan Converter) 22, an image processor 23, a display controller 24, and a display unit 25 are sequentially connected to the signal processor 21 in this order. An image memory 26 is connected to the image processor 23, and the signal processor 21, the DSC 22, the image processor 23, and the image memory 26 form an image producer 27. An apparatus body controller 28 is connected to the signal processor 21, the DSC 22, and the display controller 24, and an operating unit 29 and a storage unit 30 are connected to the apparatus body controller 28.

The probe controller 13 of the ultrasound probe 1 and the apparatus body controller 28 of the diagnostic apparatus body 2 are connected with each other.

Each of the transducers 3 transmits an ultrasonic wave in accordance with an actuation signal supplied from the transmission drive unit 6 of the transmission circuit 4, receives an ultrasonic echo from the subject, and outputs a reception signal. Each transducer 3 is constituted by a vibrator in which electrodes are formed at both ends of a piezoelectric body composed of piezoelectric ceramic represented by PZT (lead zirconate titanate), a polymer piezoelectric device, such as PVDF (polyvinylidene fluoride) or polyvinylidene fluoride-trifluoroethylene copolymer, piezoelectric single crystal represented by PMN-PT (lead magnesium niobate-lead titanate solid solution), or the like.

If a pulsed or continuous-wave voltage is applied across the electrodes of the vibrator, the piezoelectric body expands and contracts, whereby pulsed or continuous-wave ultrasonic waves are produced from the transducers and the produced ultrasonic waves are synthesized to form an ultrasonic beam. The transducers expand and contract as they receive propagating ultrasonic waves and produce electric signals, and the electric signals are output as the reception signals of the ultrasonic waves.

The transmission drive unit 6 of the transmission circuit 4 includes, for example, a plurality of pulse generators. The transmission drive unit 6 adjusts the delay amount of each of the actuation signals on the basis of a transmission delay pattern selected by the transmission controller 7 such that ultrasonic waves transmitted from the transducers 3 form a broad ultrasonic beam which covers the area of a tissue in the subject, and supplies the adjusted actuation signals to the transducers 3.

The reception signal processors 8 of the reception circuit 5 respectively perform quadrature detection or quadrature sampling on the reception signals output from the corresponding transducers 3 under the control of the reception controller 12 to produce complex baseband signals, and sample the complex baseband signals to produce sample data including information relating to the area of a tissue. The reception signal processors 8 may perform data compression for low bit rate coding on data obtained by sampling the complex baseband signals to produce sample data.

The data storage unit 9 is constituted by a memory or the like, and stores sample data for at least one frame produced by the reception signal processors 8.

The phasing adder 10 performs a reception focus process by selecting one reception delay pattern from among a plurality of reception delay patterns stored in advance in accordance with the reception direction set in the reception controller 12, giving the delay to each of a plurality of complex baseband signals represented by sample data on the basis of the selected reception delay pattern, and adding the complex baseband signals. With this reception focus process, the focus of the ultrasonic echo is narrowed down to produce a baseband signal (sound ray signal).

The reception signal correction unit 11 adjusts the reception signal processors 8 under the control of the reception controller 12 such that the reception signal obtained by each transducer 3 is corrected in accordance with the angle between a predetermined reflection point in the subject and an acoustic radiation surface in each transducer 3.

The probe controller 12 controls the respective units of the ultrasound probe 1 on the basis of various control signals transmitted from the apparatus body controller 28 of the diagnostic apparatus body 2.

The signal processor 21 of the diagnostic apparatus body 2 performs correction of attenuation depending on distance in accordance with the depth of the reflection position of the ultrasonic wave on the sound ray signal produced by the phasing adder 10 of the ultrasound probe 1, and then performs envelope detection to produce a B-mode image signal which is tomographic image information relating to the tissue in the subject.

The DSC 22 converts (raster-converts) the B-mode image signal produced by the signal processor 21 to an image signal based on a normal television signal scanning system.

The image processor 23 performs various kinds of necessary image processing, such as a gradation processing, on the B-mode image signal input from the DSC 22, and outputs the B-mode image signal to the display controller 24 or stores the B-mode image signal in the image memory 26.

The display controller 24 causes the display unit 25 to display an ultrasound diagnostic image on the basis of the B-mode image signal subjected to the image processing by the image processor 23.

The display unit 25 includes, for example, a display device, such as an LCD, and displays an ultrasound diagnostic image under the control of the display controller 24.

The operating unit 29 is used when an operator performs input operation, and may include a keyboard, a mouse, a trackball, a touch panel, and the like.

The storage unit 30 stores an operation program or the like, and a recording medium such as hard disk, flexible disk, MO, MT, RAM, CD-ROM, DVD-ROM, SD card, CF card and USB memory, or a server may be used as the storage unit 30.

The apparatus body controller 28 controls the respective units in the diagnostic apparatus body 2 on the basis of various command signals and the like input from the operating unit 29 by the operator.

Although the signal processor 21, the DSC 22, the image processor 23 and the display controller 24 are constituted by a CPU and an operation program which causes the CPU to perform various processing, these may be constituted by digital circuits.

Figure 2:
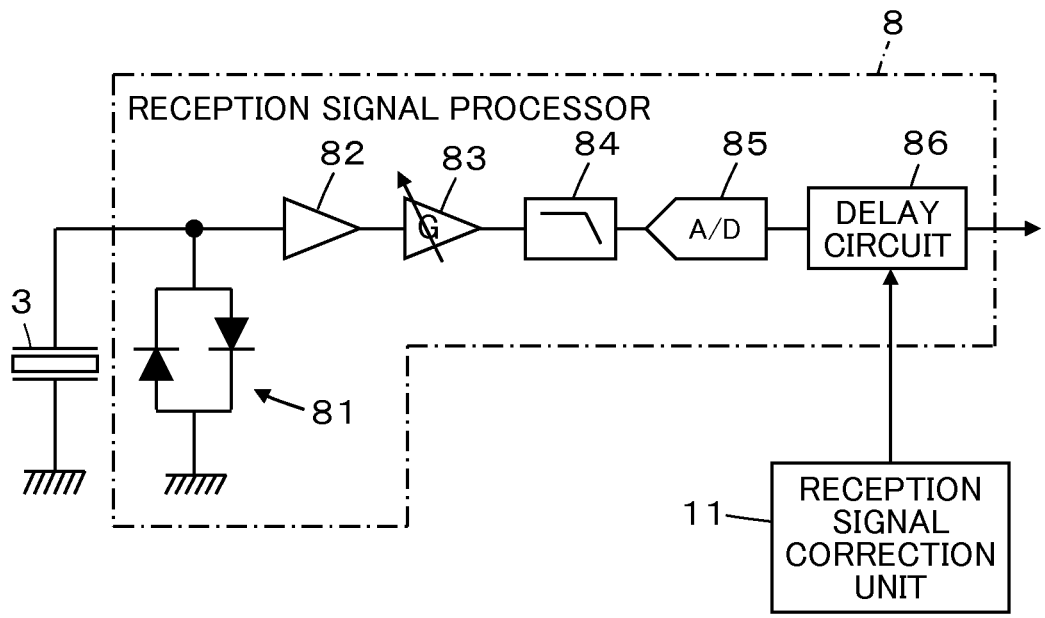
FIG. 2 is a block diagram illustrating an internal configuration of a reception signal processor used in Embodiment 1.

FIG. 2 illustrates an internal configuration of each reception signal processor 8 in the reception circuit 5 of the ultrasound probe 1. The reception signal processor 8 has an input protection circuit 81 connected to the corresponding transducer 3. A preamplifier 82 and a variable-gain amplifier 83 are sequentially connected to the input protection circuit 81, and an A/D converter 85 is connected to the variable-gain amplifier 83 through a low pass filter 84. A delay circuit 86 is connected to the A/D converter 85, and the reception signal correction unit 11 is connected to the delay circuit 86.

The input protection circuit 81 prevents the input of a signal whose voltage exceeds a set value from the transducer 3 to the preamplifier 82. The preamplifier 82 statically amplifies the reception signal output from the transducer 3, and the variable-gain amplifier 83 dynamically performs gain adjustment.

The low pass filter 84 removes a high-frequency component, which is not used for signal detection, from the reception signal amplified by the preamplifier 82 and the variable-gain amplifier 83. The A/D converter 85 converts the analog reception signal, in which a high-frequency component is removed by the low pass filter 84, to a digital signal on the basis of a conversion start signal input from the reception controller 12.

The delay circuit 86 delays the reception signal A/D converted by the A/D converter 85 by the time designated by the reception signal correction unit 11.

Figure 3:
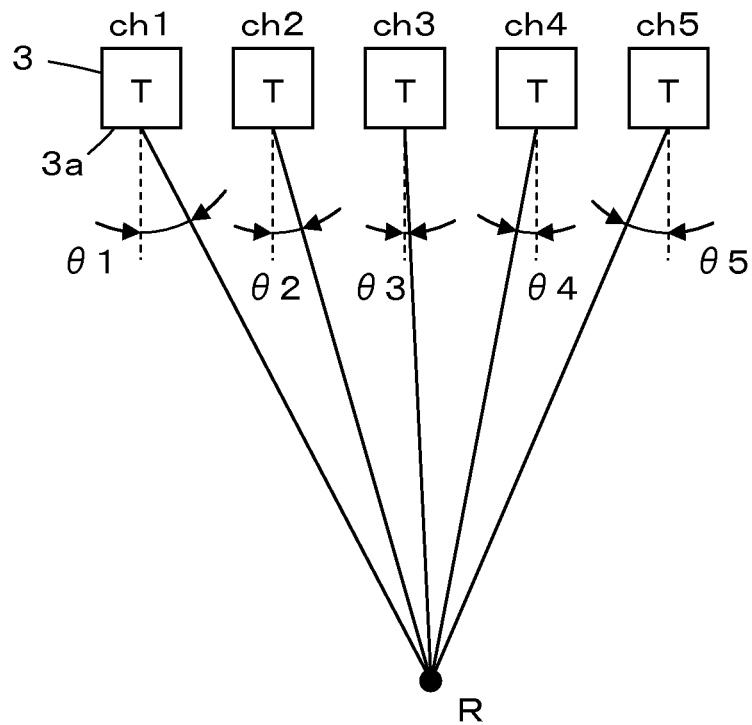
FIG. 3 is a diagram schematically illustrating a positional relationship between a reflection point in a subject and each transducer of a transducer array.

FIG. 3 illustrates a positional relationship between the transducers 3 of the ultrasound probe 1 and a predetermined reflection point R in the subject. The transducers 3 of channels ch1 to ch5 are arranged in a one-dimensional array and have acoustic radiation surfaces 3a parallel to each other, and one reflection point R is positioned to face the acoustic radiation surfaces 3a of the transducers 3. For this reason, the angle between the reflection point R and the acoustic radiation surface 3a in each transducer 3 differs between the transducers 3. That is, if the angle between a line, which connects the acoustic radiation surface 3a of the transducer 3 and the reflection point R, and a normal line to the acoustic radiation surface 3a is the angle between the reflection point R and the acoustic radiation surface 3a in the transducer 3, the angles between the acoustic radiation surfaces 3a of the transducers 3 of the channels ch1 to ch5 and the reflection point R are θ1 to θ5, respectively.

Figure 4:
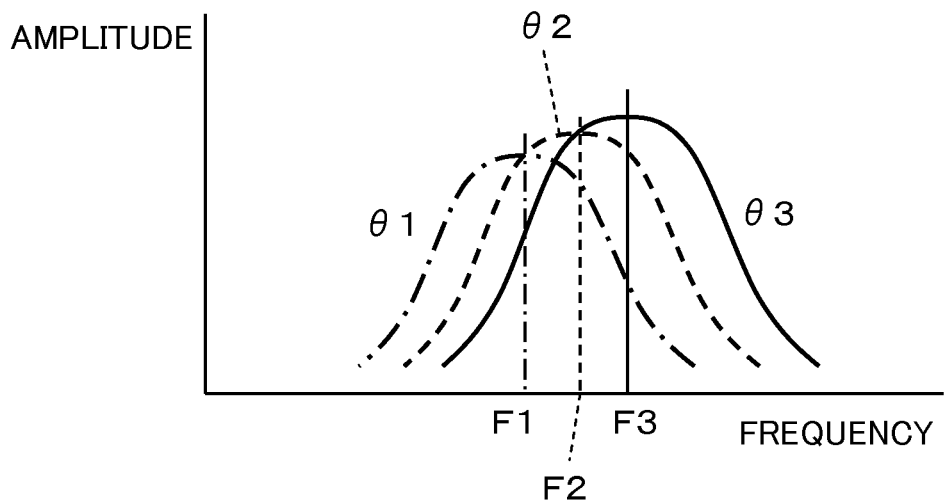
FIG. 4 is a graph illustrating a change in center frequency depending on an angle between a reflection point in a subject and an acoustic radiation surface in each transducer of a transducer array.

Since the incidence angle of the ultrasonic echo from the reflection point R differs between the transducers 3 as described above, the reception signal obtained by the transducer 3 has a different center frequency depending on the incidence angle of the ultrasonic echo. For example, as illustrated in FIG. 4, while the reception signal obtained by the transducer 3 of the channel ch3 in which the angle between the reflection point R and the acoustic radiation surface 3a is θ3 has a center frequency F3, the reception signals obtained by the transducers 3 of the channels ch2 and ch1 in which the angles are θ2 and θ1 greater than θ3 have center frequencies F2 and F1 lower than the center frequency F3 in the transducer 3 of the channel ch3.

If phase matching is performed on the reception signals having different center frequencies to produce a sound ray signal, degradation in image quality of an ultrasound image occurs. For this reason, the reception signal correction unit 11 contains an internal correction table, in which correction amounts depending on various incidence angles of the ultrasonic echo, that is, various angles between the reflection point R and the acoustic radiation surface 3a in each transducer 3 are written, and corrects the reception signals of the transducers 3 by using the correction table.

In Embodiment 1, the correction amounts written in the correction table are delay amounts for the reception signal. The reception signal correction unit 11 reads a delay amount corresponding to the angle between the reflection point R and the acoustic radiation surface 3a in each transducer 3 from the correction table, and gives a command to the delay circuit 86 of each reception signal processor 8 such that a change in the center frequency is compensated for, thereby adjusting delay with respect to the reception signal.

Next, the operation of Embodiment 1 will be described.

First, ultrasonic waves are transmitted from the transducers 3 in accordance with the actuation signals supplied from the transmission drive unit 6 of the ultrasound probe 1. The reception signal output from each transducer 3 having received the ultrasonic echo from the subject is supplied to the corresponding reception signal processor 8.

In each reception signal processor 8, the reception signal passes through the input protection circuit 81 of the reception signal processor 8, is amplified by the preamplifier 82 and the variable-gain amplifier 83, and after an unnecessary high-frequency component is removed therefrom by the low pass filter 84, the reception signal is A/D converted by the A/D converter 85. At this time, while the center frequency of the reception signal which is supplied to each reception signal processor 8 differs due to a difference in the incidence angle of the ultrasonic echo on the acoustic radiation surface 3a of each transducer 3, the reception signal correction unit 11 adjusts the delay with respect to the reception signal referring to the correction table and using the delay circuit 86 of each reception signal processor 8 in accordance with the angle between the reflection point in the subject and the acoustic radiation surface 3a in each transducer 3 such that a change in the center frequency is compensated for. The reception signal A/D converted by the A/D converter 85 is output as sample data after delay is adjusted by the delay circuit 86.

The thus-produced sample data is stored in the data storage unit 9. Sample data for one frame is read from the data storage unit 9, and, after a sound ray signal is produced by the phasing adder 10, an image signal is produced by the image producer 27 of the diagnostic apparatus body 2. Subsequently, on the basis of the image signal, an ultrasound image is displayed on the display unit 25 by the display controller 24.

As described above, delay with respect to the reception signal output from each transducer 3 is adjusted in conformity with a change in the center frequency depending on the angle between the reflection point in the subject and the acoustic radiation surface 3a in each transducer 3. Accordingly, it is possible to suppress degradation in image quality of an ultrasound image due to a difference in the incidence angle of the ultrasonic echo on the acoustic radiation surface 3a of each transducer 3, making it possible to produce a high-image-quality ultrasound image.

In particular, when diagnosing a superficial tissue of a subject at a short distance from the transducer array of the ultrasound probe 1, the angle between the reflection point and the acoustic radiation surface 3a in each transducer 3 largely changes between the transducers 3. Accordingly, the correction effect of the reception signal by the reception signal correction unit 11 becomes prominent, thereby considerably improving image quality.

Since the measurement depth up to the reflection point differs between the transducers 3 depending on the angle between the reflection point in the subject and the acoustic radiation surface 3a in each transducer 3, attenuation of an ultrasonic wave also differs between the transducers 3. For this reason, it is desirable that the reception signal correction unit 11 adjusts the delay with respect to the reception signal taking into consideration a change in frequency due to a change in attenuation of an ultrasonic wave.

Embodiment 2

Although in Embodiment 1 described above, the delay amount for the reception signal is used as the correction amount, and the reception signal correction unit 11 adjusts the delay with respect to the reception signal by the delay circuit 86 of the reception signal processor 8 in accordance with the angle between the reflection point R and the acoustic radiation surface 3a in each transducer 3, the invention is not limited thereto. For example, transmission filter characteristics for the reception signal may be adjusted in accordance with the angle between the reflection point R and the acoustic radiation surface 3a in each transducer 3.

Figure 5:
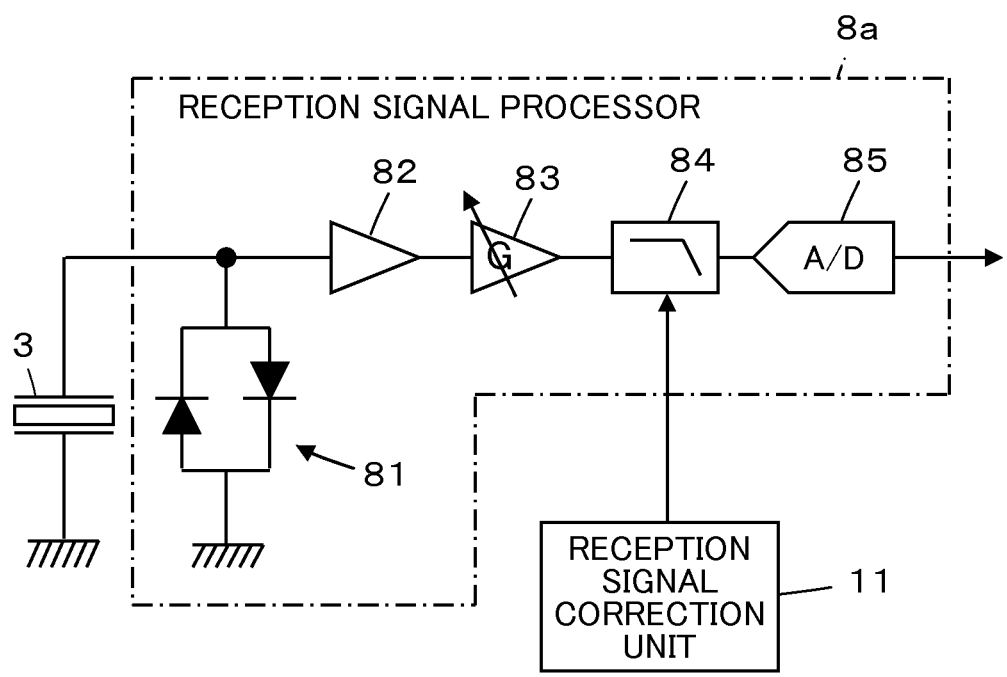
FIG. 5 is a block diagram illustrating an internal configuration of a reception signal processor used in Embodiment 2.

FIG. 5 illustrates an internal configuration of each reception signal processor 8a in a reception circuit 5 according to Embodiment 2. As compared with the reception signal processor 8 used in Embodiment 1 illustrated in FIG. 2, the reception signal processor 8a is not provided with the delay circuit 86, and the reception signal correction unit 11 is connected to the low pass filter 84.

An ultrasound diagnostic apparatus according to Embodiment 2 has the same configuration as the ultrasound diagnostic apparatus according to Embodiment 1 illustrated in FIG. 1, except that the reception signal processor 8a is used instead of the reception signal processor 8.

The reception signal correction unit 11 contains a correction table in which transmission filter characteristics depending on the angle between the reflection point R and the acoustic radiation surface 3a in each transducer 3 are written as the correction amount and corrects the reception signals obtained by the transducers 3 using the correction table.

During operation, the reception signal output from each transducer 3 having received the ultrasonic echo from the subject passes through the input protection circuit 81 of the corresponding reception signal processor 8a, is amplified by the preamplifier 82 and the variable-gain amplifier 83, and is input to the low pass filter 84. While the center frequency of the reception signal supplied to each reception signal processor 8a differs due to a difference in the incidence angle of the ultrasonic echo on the acoustic radiation surface 3a of each transducer 3, the reception signal correction unit 11 adjusts the transmission filter characteristics in the low pass filter 84 in accordance with the angle between the reflection point in the subject and the acoustic radiation surface 3a in each transducer 3 with reference to the correction table such that a change in the center frequency is compensated for. The reception signal passes through the low pass filter 84, is A/D converted by the A/D converter 85, and is then output as sample data.

A sound ray signal is produced on the basis of the thus-produced sample data by the phasing adder 10, an image signal is produced by the image producer 27 of the diagnostic apparatus body 2, and an ultrasound image is displayed on the display unit 25 by the display controller 24.

As described above, even when the transmission filter characteristics for the reception signal output from each transducer 3 are adjusted in conformity with a change in the center frequency depending on the angle between the reflection point in the subject and the acoustic radiation surface 3a in each transducer 3, it is possible to suppress degradation in image quality of an ultrasound image due to a difference in the incidence angle of the ultrasonic echo on the acoustic radiation surface 3a of each transducer 3, thereby producing a high-image-quality ultrasound image.

The reception signal correction unit 11 may adjust the upper limit frequency, the lower limit frequency, the bandwidth, and the like of a pass band in the low pass filter 84 as the transmission filter characteristics.

Since the measurement depth up to the reflection point differs between the transducers 3 depending on the angle between the reflection point in the subject and the acoustic radiation surface 3a in each transducer 3, attenuation in an ultrasonic wave also differs between the transducers 3. For this reason, it is desirable that the reception signal correction unit 11 adjusts the transmission filter characteristics for the reception signal taking into consideration a change in frequency due to a change in attenuation of an ultrasonic wave.

Embodiment 3

Figure 6:
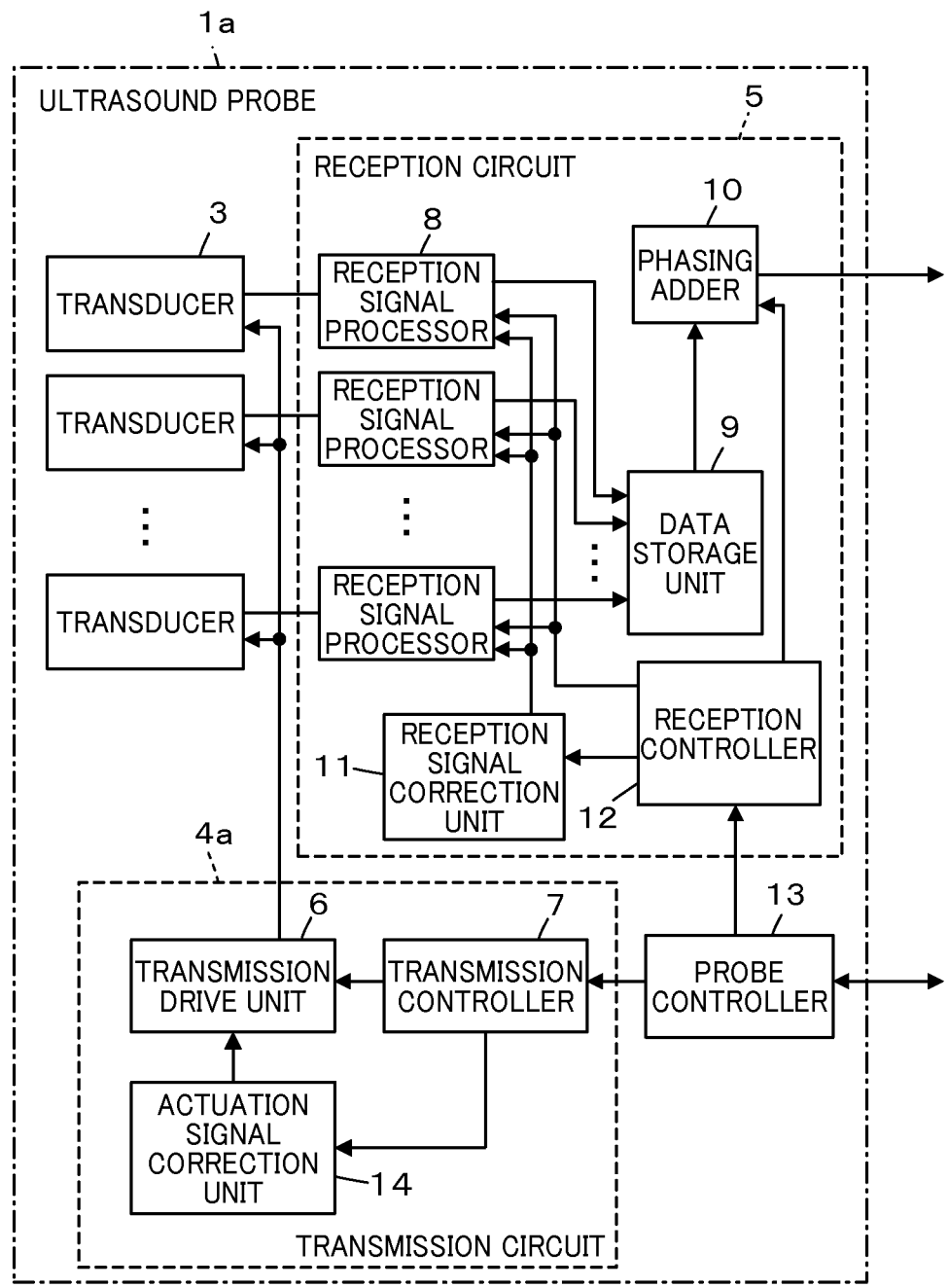
FIG. 6 is a block diagram illustrating an internal configuration of an ultrasound probe in Embodiment 3.

FIG. 6 illustrates an internal configuration of an ultrasound probe 1a used in Embodiment 3. The ultrasound probe 1a uses a transmission circuit 4a having an actuation signal correction unit 14 therein instead of the transmission circuit 4 in the ultrasound probe 1 which is used in Embodiment 1 illustrated in FIG. 1, and is connected to the diagnostic apparatus body 2 illustrated in FIG. 1 for use.

In the transmission circuit 4a, the actuation signal correction unit 14 is connected to the transmission drive unit 6, and the transmission controller 7 is connected to the actuation signal correction unit 14.

Under the control of the transmission controller 7, the actuation signal correction unit 14 adjusts the waveform of an actuation signal supplied from the transmission drive unit 6 to each transducer 3 in accordance with a change in the center frequency depending on the angle between the reflection point in the subject and the acoustic radiation surface 3a in each transducer 3 such that the change in the center frequency is compensated for.

The actuation signal correction unit 14 contains a correction table in which waveform adjustment amounts depending on various angles between the reflection point and the acoustic radiation surface 3a in the transducer 3 are written. The actuation signal correction unit 14 reads the waveform adjustment amount corresponding to the angle between the reflection point and the acoustic radiation surface 3a in each transducer 3 from the correction table and gives a command to the transmission drive unit 6 to adjust the waveform of the actuation signal.

By providing the actuation signal correction unit 14 to adjust the waveform of the actuation signal, it is possible to suppress degradation in image quality of an ultrasound image due to a difference in the incidence angle of the ultrasonic echo on the acoustic radiation surface 3a of each transducer 3, making it possible to produce a higher-image-quality ultrasound image.

Embodiment 4

Figure 7:
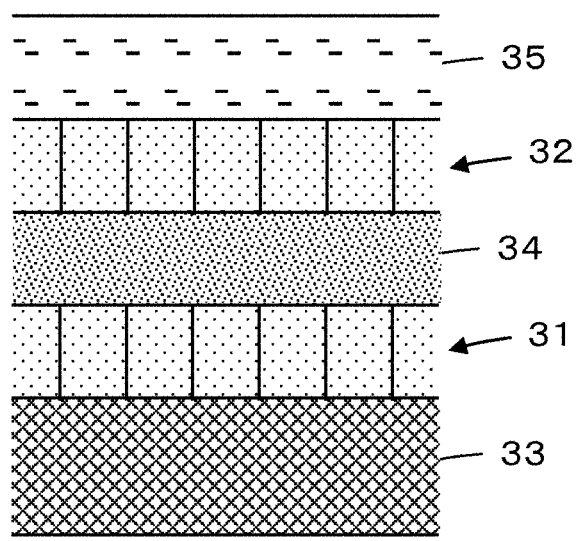
FIG. 7 is a partial sectional view illustrating a structure of an ultrasound transducer unit used in Embodiment 4.

Although in Embodiments 1 to 3 described above, the ultrasound probe 1 or 1a has one transducer array composed of the transducers 3 as an ultrasound transducer unit, as illustrated in FIG. 7, an ultrasound transducer unit which includes a first transducer array 31 composed of a plurality of inorganic piezoelectric devices and a second transducer array 32 composed of a plurality of organic piezoelectric devices may be used.

The first transducer array 31 is formed on a surface of a backing member 33, the second transducer array 32 is formed on the first transducer array 31 through an acoustic matching layer 34, and an acoustic lens 35 is bonded onto the second transducer array 32.

Each inorganic piezoelectric device of the first transducer array 31 has an inorganic piezoelectric body formed of piezoelectric ceramic represented by lead zirconate titanate (PZT) or piezoelectric single crystal represented by lead magnesium niobate-lead titanate solid solution (PMN-PT). Each organic piezoelectric device of the second transducer array 32 has an organic piezoelectric body formed of a polymer piezoelectric device, such as polyvinylidene fluoride (PVDF) or polyvinylidene fluoride-trifluoroethylene copolymer.

For example, an ultrasonic wave is transmitted from the first transducer array 31 toward the subject, and an ultrasonic echo from the subject is received by the second transducer array 32 or by both the first transducer array 31 and the second transducer array 32.

The reception characteristics differ between the inorganic piezoelectric devices and the organic piezoelectric devices, and with the use of the second transducer array 32 having the plurality of organic piezoelectric devices, it is possible to receive harmonic components with high precision.

When this ultrasound transducer unit is used, it is desirable that the reception signal correction unit 11 has a first correction table created corresponding to the first transducer array 31 and a second correction table created corresponding to the second transducer array 32. Correction amounts referenced from the first correction table are applied to the first transducer array 31, and correction amounts referenced from the second correction table are applied to the second transducer array 32 in a separate manner.

When the ultrasound transducer unit shown in FIG. 7 is used in Embodiment 3, it is desirable that the actuation signal correction unit 14 has also one correction table created corresponding to the first transducer array 31 and another correction table created corresponding to the second transducer array 32 separately.

Furthermore, the correction table used in Embodiments 1 to 4 described above may be actually created on the basis of data measured while changing the angle between the predetermined reflection point and the acoustic radiation surface 3a in each transducer 3 or may be created through calculation taking into consideration angle dependence of the center frequency.

Since the angle between the reflection point in the subject and the acoustic radiation surface 3a in each transducer 3 depends largely on the depth of a measurement region in a subject where there is a reflection point, a correction table may be created for each representative measurement region, and a correction table may be selected and used in conformity with a measurement region relating to diagnosis.

The connection of the ultrasound probe 1 or 1a and the diagnostic apparatus body 2 may be either wired connection or connection by wireless communication.

What is claimed is:

1. An ultrasound diagnostic apparatus comprising:
a transducer array having a plurality of transducers arranged in an array;
a transmission circuit which supplies an actuation signal to each transducer of the transducer array to transmit an ultrasonic wave toward a subject; a plurality of reception signal processors corresponding to the plurality of transducers, each of the plurality of reception signal processors including a delay circuit which delays a reception signal output from a corresponding transducer to output a delayed reception signal as sample data;
a reception signal correction hardware processing unit configured to impart a delay amount which compensates for a change in center frequency corresponding to an angle between the reflection point and the acoustic radiation surface in each transducer in order to delay the reception signal output from each transducer by the delay amount with the delay circuit in each reception signal processor to make the center frequency of the reception signal output from each transducer constant;
a phasing adder which produces a sound ray signal through phasing addition of sample data output from the plurality of reception signal processors; and
an image producer which produces an ultrasound image on the basis of the sound ray signal produced by the phasing adder.

2. The ultrasound diagnostic apparatus according to claim 1,
wherein the reception signal correction unit adjusts a delay taking into consideration a change in frequency due to a change in attenuation caused by a difference in measurement depth depending on the angle between the reflection point and the acoustic radiation surface in each transducer.

3. The ultrasound diagnostic apparatus according to claim 1,
wherein the transducer array includes a first transducer array composed of a plurality of inorganic piezoelectric devices and a second transducer array composed of a plurality of organic piezoelectric devices, and
wherein the reception signal correction unit corrects the reception signal by using different correction tables between the first transducer array and the second transducer array.

4. An ultrasound diagnostic apparatus comprising:
a transducer array having a plurality of transducers arranged in an array;
a transmission circuit which supplies an actuation signal to each transducer of the transducer array to transmit an ultrasonic wave toward a subject;
a plurality of reception signal processors corresponding to the plurality of transducers, each of the plurality of reception signal processors including a low pass filter which removes a high-frequency component from a reception signal output from a corresponding transducer to output as sample data a reception signal in which a high-frequency component is removed;
a reception signal correction hardware processing unit configured to impart a correction amount which comprises a transmission filter characteristic for the reception signal output from each transducer, the correction amount compensating for a change in center frequency depending on an angle between the reflection point and the acoustic radiation surface in each transducer and a change in frequency due to a change in attenuation caused by a difference in a measurement depth depending on the angle between the reflection point and the acoustic radiation surface in each transducer in order to adjust a transmission filter characteristic of the low pass filter in each reception signal processor for the reception signal output from each transducer by the correction amount to make the center frequency of the reception signal output from each transducer constant;
a phasing adder which produces a sound ray signal through phasing addition of sample data output from the plurality of reception signal processors; and an image producer which produces an ultrasound image on the basis of the sound ray signal produced by the phasing adder.

5. The ultrasound diagnostic apparatus according to claim 4, wherein the transducer array includes a first transducer array composed of a plurality of inorganic piezoelectric devices and a second transducer array composed of a plurality of organic piezoelectric devices, and wherein the reception signal correction unit corrects the reception signal by using different correction tables between the first transducer array and the second transducer array.

6. An ultrasound diagnostic apparatus comprising:
a transducer array having a plurality of transducers arranged in an array;
a transmission circuit which supplies an actuation signal to each transducer of the transducer array to transmit an ultrasonic wave toward a subject;
an actuation signal correction hardware processing unit configured to impart a correction amount which comprises a waveform adjustment amount for the actuation signal supplied to each transducer which compensates for a change in center frequency depending on an angle between the reflection point and the acoustic radiation surface in each transducer in order to adjust a waveform of the actuation signal supplied to each transducer from the transmission circuit by the correction amount to make the center frequency of the reception signal output from each transducer constant;
a plurality of reception signal processors corresponding to the plurality of transducers, each of the plurality of reception signal processors processing a reception signal output from a corresponding transducer to output a processed reception signal as sample data;
a phasing adder which produces a sound ray signal through phasing addition of sample data output from the plurality of reception signal processors; and
an image producer which produces an ultrasound image on the basis of the sound ray signal produced by the phasing adder.

7. The ultrasound diagnostic apparatus according to claim 6, wherein the transducer array includes a first transducer array composed of a plurality of inorganic piezoelectric devices and a second transducer array composed of a plurality of organic piezoelectric devices, and wherein the actuation signal correction unit corrects the actuation signal supplied to each transducer by using different correction tables between the first transducer array and the second transducer array.

* * * * *